US012714861B2

(12) United States Patent
Marnfeldt

(10) Patent No.: US 12,714,861 B2
(45) Date of Patent: Aug. 25, 2026

(54) METHOD AND APPARATUS FOR DITHERING NEUROSTIMULATION PARAMETERS

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 428 days.

(21) Appl. No.: 18/208,473

(22) Filed: Jun. 12, 2023

(65) Prior Publication Data

US 2023/0405331 A1 Dec. 21, 2023

Related U.S. Application Data

(60) Provisional application No. 63/353,518, filed on Jun. 17, 2022.

(51) Int. Cl.

*A61N 1/36* (2006.01)
*A61N 1/02* (2006.01)
*A61N 1/372* (2006.01)

(52) U.S. Cl.

CPC ......... *A61N 1/36192* (2013.01); *A61N 1/025* (2013.01); *A61N 1/36139* (2013.01); *A61N 1/36175* (2013.01); *A61N 1/37247* (2013.01)

(58) Field of Classification Search

CPC ................ A61N 1/36192; A61N 1/025; A61N 1/36139; A61N 1/36175; A61N 1/37247;

(Continued)

(56) References Cited

U.S. PATENT DOCUMENTS 5,350,414 A * 9/1994 Kolen .................... A61N 1/025 607/62
9,872,990 B2 1/2018 Parker et al.

(Continued)

FOREIGN PATENT DOCUMENTS

WO WO-2023244524 A1 12/2023

OTHER PUBLICATIONS

"European Application Serial No. 23739713.8, Response to Communication pursuant to Rules 161 and 162 EPC filed", 12 pgs.

(Continued)

*Primary Examiner* — Carl H Layno
*Assistant Examiner* — Dhrasti S. Dalal
(74) *Attorney, Agent, or Firm* — Schwegman Lundberg & Woessner, P.A.

(57) ABSTRACT

An example of a system for delivering neurostimulation pulses includes a stimulation output circuit setting a hardware resolution for each stimulation parameter. A control circuit may be configured to receive the stimulation parameters and may include a dithering mode enabler configured to enable a dithering mode and a parameter dithering processor configured to operate when the dithering mode is enabled. The parameter dithering processor may be configured to identify a received stimulation parameter to be dithered and to dither a received value of the identified stimulation parameter by programming the stimulation output circuit to deliver pulses at a higher value of the identified stimulation parameter interleaved with pulses at a lower value of the identified parameter at a ratio determined for producing an average value approximating to the received value. The higher value and the lower value are values available with the hardware resolution.

20 Claims, 11 Drawing Sheets

(58) Field of Classification Search
CPC .............. A61N 1/3615; A61N 1/36125; A61N 1/36146
See application file for complete search history.

(56) References Cited

U.S. PATENT DOCUMENTS

| | | | | |
|---|---|---|---|---|
| 10,668,288 | B2 | 6/2020 | De Ridder | |
| 2013/0318259 | A1* | 11/2013 | Sherman ............ | A61N 1/36071 710/25 |
| 2016/0008604 | A1 | 1/2016 | Doan et al. | |
| 2018/0056073 | A1 | 3/2018 | Torgerson | |
| 2018/0272133 | A1 | 9/2018 | Kibler et al. | |
| 2019/0366107 | A1 | 12/2019 | Moffitt | |
| 2020/0179703 | A1* | 6/2020 | Bourget et al. ........ | A61N 1/025 |
| 2020/0398057 | A1 | 12/2020 | Esteller et al. | |
| 2022/0062643 | A1* | 3/2022 | De Ridder ......... | A61N 1/36071 |
| 2024/0408397 | A1* | 12/2024 | Esteller et al. ...... | A61N 1/3606 |

OTHER PUBLICATIONS

"International Application Serial No. PCT/US2023/025029, International Preliminary Report on Patentability mailed Dec. 26, 2024", 8 pgs.

"International Application Serial No. PCT/US2023/025029, International Search Report mailed Nov. 9, 2023", 4 pgs.

"International Application Serial No. PCT/US2023/025029, Written Opinion mailed Nov. 9, 2023", 6 pgs.

* cited by examiner

METHOD AND APPARATUS FOR DITHERING NEUROSTIMULATION PARAMETERS

CLAIM OF PRIORITY

This application claims the benefit of U.S. Provisional Application No. 63/353,518, filed on Jun. 17, 2022, which is hereby incorporated by reference in its entirety.

TECHNICAL FIELD

This document relates generally to neurostimulation and more particularly to a system that provides for increased resolution in controlling delivery of neurostimulation by dithering stimulation parameters.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical pulses. The delivery is controlled using stimulation parameters that specify spatial (where to stimulate), temporal (when to stimulate), and informational (patterns of pulses directing the nervous system to respond as desired) aspects of the electrical pulses. Range and resolution for each of these stimulation parameters depends on precision needed or desired for each type of neurostimulation therapy. For example, certain types of therapies, particularly those employing low levels of stimulation intensity, may require a fine resolution for each of one or more of the stimulation parameters to achieve a desired level of precision in therapy control. A neurostimulation system including the implantable neurostimulator and the external programming device) needs to accommodate such need for high-resolution in controlling the stimulation parameters.

SUMMARY

An example (e.g., "Example 1") of a system for delivering neurostimulation from a stimulation output circuit according to stimulation parameters defining a pattern of neurostimulation pulses is provided. The stimulation output circuit sets a hardware resolution for each parameter of the stimulation parameters and includes timers each independently programmable for controlling timing of one or more pulses of the pattern of neurostimulation pulses. The system includes a control circuit that may be configured to receive the stimulation parameters and to control operation of the stimulation output circuit using the received stimulation parameters. The control circuit may include a dithering mode enabler and a parameter dithering processor. The dithering mode enabler may be configured to enable a dithering mode. The parameter dithering processor may be configured to operate when the dithering mode is enabled, to identify a stimulation parameter from the received stimulation parameters to be dithered, and to dither a received value of the identified stimulation parameter by programming the stimulation output circuit to deliver neurostimulation pulses at a higher value of the identified stimulation parameter interleaved with neurostimulation pulses at a lower value of the identified parameter at a ratio determined for producing an average value approximating to the received value. The received value of the identified stimulation parameter is not available with the hardware resolution. The higher value and the lower value are values of the identified stimulation parameter that are available with the hardware resolution.

In Example 2, the subject matter of Example 1 may optionally be configured such that the dithering mode enabler is configured to determine whether parameter dithering is needed and to enable the dithering mode in response to the determination that the parameter dithering is needed.

In Example 3, the subject matter of Example 2 may optionally be configured such that the dithering mode enabler is configured to determine whether the hardware resolution is sufficient for values of the received stimulation parameters without enabling the dithering mode and to enable the dithering mode in response to the determination that the hardware resolution is not sufficient for at least one value of the received stimulation parameters without enabling the dithering mode.

In Example 4, the subject matter of Example 3 may optionally be configured such that the dithering mode enabler is configured to determine a desirable maximum relative step size for each stimulation parameter of the received stimulation parameters based on received values of that stimulation parameter and to determine whether the hardware resolution is sufficient for the determined desirable maximum relative step sizes of all the received stimulation parameters.

In Example 5, the subject matter of any one or any combination of Examples 3 and 4 may optionally be configured such that the dithering mode enabler is configured to determine whether the hardware resolution is sufficient for the values of the received stimulation parameters with the dithering mode enabled and to enable the dithering mode in response to the determination that the hardware resolution is not sufficient for at least one value of the received stimulation parameters without enabling the dithering mode and a determination that the hardware resolution is sufficient for the values of the received stimulation parameters with the dithering mode enabled.

In Example 6, the subject matter of Example 5 may optionally be configured such that the dithering mode enabler is configured to generate an indication of a need for modifying one or more values of the stimulation parameters in response to the determination that the hardware resolution is not sufficient for at least one value of the received stimulation parameters with the dithering mode enabled.

In Example 7, the subject matter of any one or any combination of Examples 1 to 6 may optionally be configured such that the dithering mode enabler is configured to allow for a selection of a parameter dithering option and to enable the dithering mode in response to the selection of the parameter dithering option.

In Example 8, the subject matter of Example 7 may optionally be configured to further include a user interface including a presentation device and a user input device, and such that the dithering mode enabler is configured to present the parameter dithering option using the presentation device, receive a selection of the parameter dithering option using the user input device, and enable the dithering mode in response to the selection of the parameter dithering option being received.

In Example 9, the subject matter of any one or any combination of Examples 7 and 8 may optionally be configured such that the dithering mode enabler is configured to allow for a deselection of the dithering option and to disable the dithering mode in response to the deselection of the parameter dithering option.

In Example 10, the subject matter of any one or any combination of Examples 7 to 9 may optionally be configured such that the dithering mode enabler is configured to enable the dithering mode in response to the determination that the parameter dithering is needed and the selection of the parameter dithering option.

In Example 11, the subject matter of Example 10 may optionally be configured such that the dithering mode enabler is configured to allow for the selection of the parameter dithering option in response to the determination that the parameter dithering is needed.

In Example 12, the subject matter of any one or any combination of Examples 1 to 11 may optionally be configured such that the parameter dithering processor is configured to determine the ratio being a function of a number of the timers used to control the delivery of the neurostimulation pulses using the identified stimulation parameter when the dithering mode is enabled.

In Example 13, the subject matter of Example 12 may optionally be configured such that the parameter dithering processor is configured to determine a desirable maximum relative step size for the identified stimulation parameter, to determine a minimum number of the timers required based on the determined desirable maximum relative step size for the identified stimulation parameter and the hardware resolution, and to set the ratio based on the determined minimum number of the timers.

In Example 14, the subject matter of Example 13 may optionally be configured such that the parameter dithering processor is configured to determine the minimum number of the timers by determining breaking points at which a step size for the identified obtained using a given number of the timers exceeds the desirable maximum relative step size for the identified stimulation parameter. The breaking points each indicate a need for an additional timer.

In Example 15, the subject matter of any one or any combination of Examples 1 to 14 may optionally be configured to include an implantable stimulator and an external programmer. The implantable stimulation includes the stimulation output circuit. The external programmer is configured to program the implantable stimulator via a wireless communication link and includes at least portions of the control circuit.

An example (e.g., "Example 16") of a method for delivering neurostimulation from a stimulation output circuit according a pattern of neurostimulation pulses is also provided. The method may include receiving stimulation parameters defining the pattern of neurostimulation pulses, determining whether to enable a dithering mode using one or more criteria, enabling the dithering mode when the one or more criteria are met, and processing the received stimulation parameters using a processor. The processing when the dithering mode is enabled may include identifying a stimulation parameter from the received stimulation parameters to be dithered and dithering a received value of the identified stimulation parameter by programming the stimulation output circuit to deliver neurostimulation pulses at a higher value of the identified stimulation parameter interleaved with neurostimulation pulses at a lower value of the identified parameter at a ratio determined for producing an average value approximating to the received value. The received value of the identified stimulation parameter is not available with a hardware resolution set by the stimulation output circuit for each parameter of the received stimulation parameters. The higher value and the lower value are values of the identified stimulation parameter that are available with the hardware resolution. The method may further include controlling operation of the stimulation output circuit using the processed stimulation parameters.

In Example 17, the subject matter of determining whether to enable the dithering mode as found in Example 16 may optionally include determining whether parameter dithering is needed.

In Example 18, the subject matter of determining whether the parameter dithering is needed set as found in Example 17 may optionally include determining whether the hardware resolution is sufficient for all values of each stimulation parameter of the received stimulation parameters without enabling the dithering mode.

In Example 19, the subject matter of determining whether to enable the dithering mode as found in Example 18 may optionally include determining whether the hardware resolution is sufficient for all values of each stimulation parameter of the received stimulation parameters with the dithering mode enabled.

In Example 20, the subject matter of determining whether to enable the dithering mode as found in any one or any combination of Examples 16 to 19 may optionally include determining whether a parameter dithering option is selected by a user.

In Example 21, the subject matter of enabling the dithering mode as found in Example 20 may optionally include enabling the dithering mode in response to the determination that the parameter dithering is needed and the determination that the parameter dithering option is selected by the user.

In Example 22, the subject matter of any one or any combination of Examples 16 to 21 may optionally further include determining the ratio as a function of a number of timers used to control the delivery of the neurostimulation pulses using the identified stimulation parameter when the dithering mode is enabled. The timers are part of the stimulation output circuit and are each independently programmable for controlling timing of one or more pulses of the pattern of neurostimulation pulses.

In Example 23, the subject matter of determining the ratio as found in Example 22 may optionally include determining a desirable maximum relative step size for the identified stimulation parameter, determining a minimum number of the timers required based on the determined desirable maximum relative step size for the identified stimulation parameter and the hardware resolution, and setting the ratio based on the determined minimum number of the timers.

An example (e.g., "Example 24") of a non-transitory computer-readable storage medium including instructions, which when executed by a system, cause the system to perform a method for delivering neurostimulation from a stimulation output circuit according a pattern of neurostimulation pulses is also provided. The method may include receiving stimulation parameters defining the pattern of neurostimulation pulses, determining whether to enable a dithering mode using one or more criteria, enabling the dithering mode when the one or more criteria are met, and processing the received stimulation parameters using a processor. The processing when the dithering mode is enabled may include identifying a stimulation parameter from the received stimulation parameters to be dithered and dithering a received value of the identified stimulation parameter by programming the stimulation output circuit to deliver neurostimulation pulses at a higher value of the identified stimulation parameter interleaved with neurostimulation pulses at a lower value of the identified parameter at a ratio determined for producing an average value approximating to the received value. The received value of the identified stimulation parameter is not available with a hardware resolution set by the stimulation output circuit for each parameter of the received stimulation parameters. The higher value and the lower value are values of the identified stimulation parameter that are available with the hardware resolution. The method may further include controlling operation of the stimulation output circuit using the processed stimulation parameters.

In Example 25, the subject matter of determining whether to enable the dithering mode as found in Example 24 may optionally include at least one of determining whether parameter dithering is needed or whether a parameter dithering option is selected by a user.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
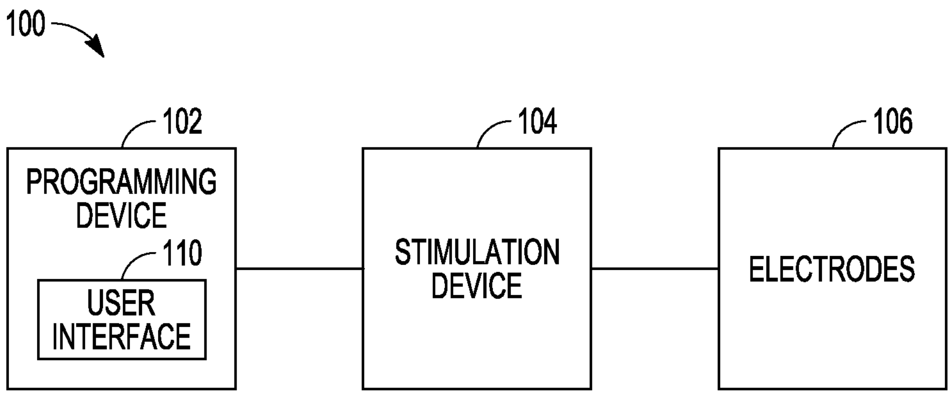
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to “an”, “one”, or “various” embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for increasing resolution in programming a therapy by dithering one or more therapy parameters. The therapy includes a neurostimulation therapy that can be delivered from a neurostimulation system and controlled using stimulation parameters. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. While DBS is specifically discussed as an example, the present subject matter can be applied in various neurostimulation therapies in which neural signals including evoked potentials are sensed.

The resolution with which the neurostimulation therapy can be programmed is limited by hardware of the stimulation device (e.g., the implantable device) used to deliver the therapy. For example, a current implantable device provides for a resolution of 100 μA for a pulse amplitude and 10 λs has for a pulse width in programming neurostimulation pulses, while for certain therapies that employ low-intensity stimulation, such as DBS, VNS, and possibly PNS, a resolution being a fraction (e.g., tens of present) of these values are desirable. Improvement of such resolution by modifying the hardware of the implantable device can be costly in terms of power consumption and/or space needed for additional circuitry.

The present subject matter can increase the resolution provided by the existing hardware of a stimulation device (e.g., an implantable device), i.e., without modifying the hardware of that stimulation device. This is achieved, using a programming device of the stimulation device (e.g., an external device for programming the implantable device), by "dithering" to produce an average value of a stimulation parameter by interleaving a higher value with a lower value at a calculated ratio. The higher value and the lower values are values directly available with the hardware limitations, and the average value represents a desirable value that is not directly available with the hardware limitations. In this manner, a resolution that can be substantially finer than the resolution limited by the hardware of the stimulation device can be achieved.

While pulse amplitude and pulse width are specifically discussed as examples of stimulation parameters, the present subject matter can be applied to other stimulation parameters, such as pulse frequency. While neurostimulation is specifically discussed as an example, the present subject matter can also be applied to programming of other therapies in which improvement of parameter resolution without modifying therapy delivery hardware is desired.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who examiners and/or treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for DBS applications. Such DBS configuration includes various features that may simplify the task of the user in programming stimulation device 104 for delivering DBS to the patient, such as the features discussed in this document.

Figure 2:
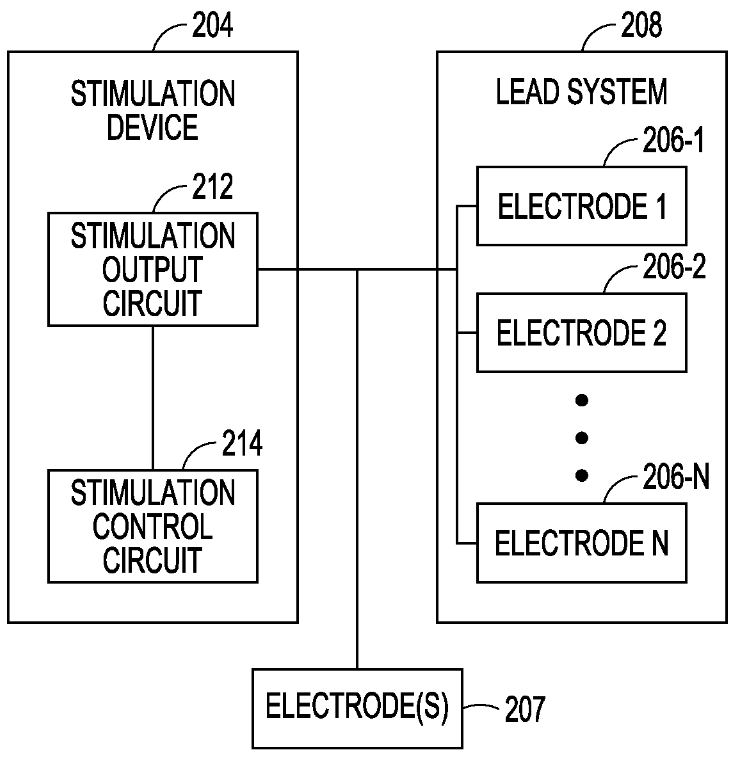
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N>2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
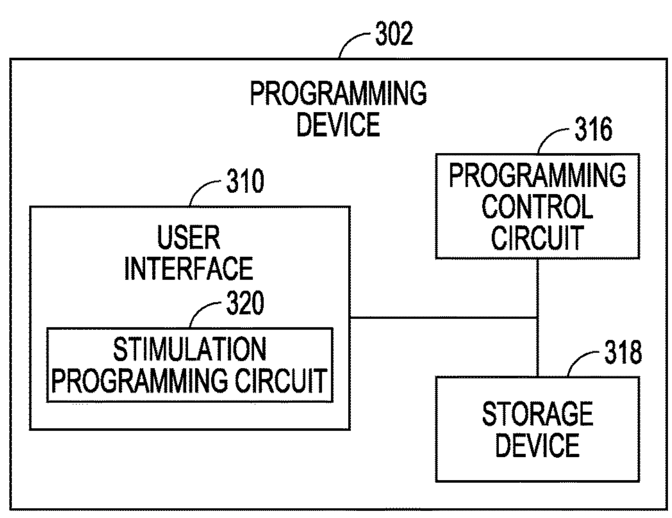
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Programming control circuit 316 generates the plurality of stimulation parameters that controls the delivery of the neurostimulation pulses according to a specified stimulation configuration that can define, for example, stimulation waveform and electrode configuration. User interface 310 represents an embodiment of user interface 110 and includes a stimulation programming circuit 320. Storage device 318 stores information used by programming control circuit 316 and stimulation programming circuit 320, such as information about a stimulation device that relates the stimulation configuration to the plurality of stimulation parameters and information relating the stimulation configuration to a volume of activation in the patient. In various embodiments, stimulation programming circuit 320 can be configured to support one or more functions allowing for programming of stimulation devices, such as stimulation device 104 including its various embodiments as discussed in this document, to control delivery of neurostimulation pulses using stimulation parameters with parameter dithering according to the present subject matter, as further discussed below with reference to FIGS. 9-14.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation configuration" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

Figure 4:
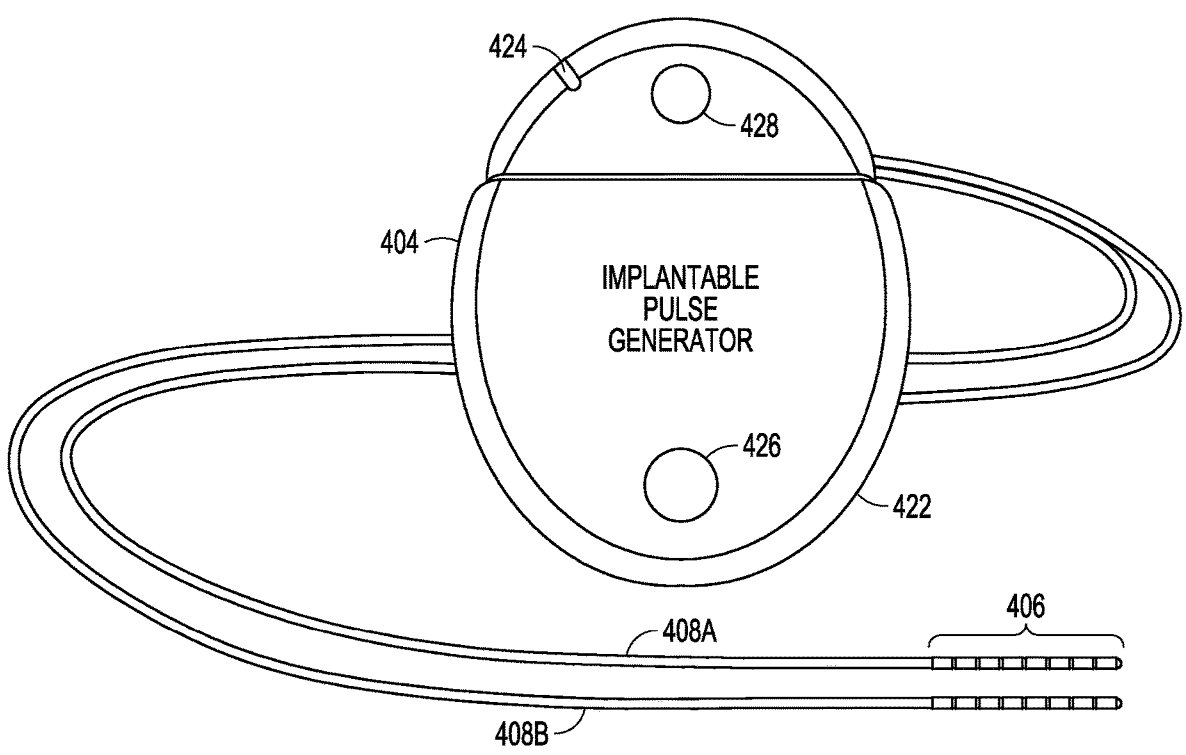
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
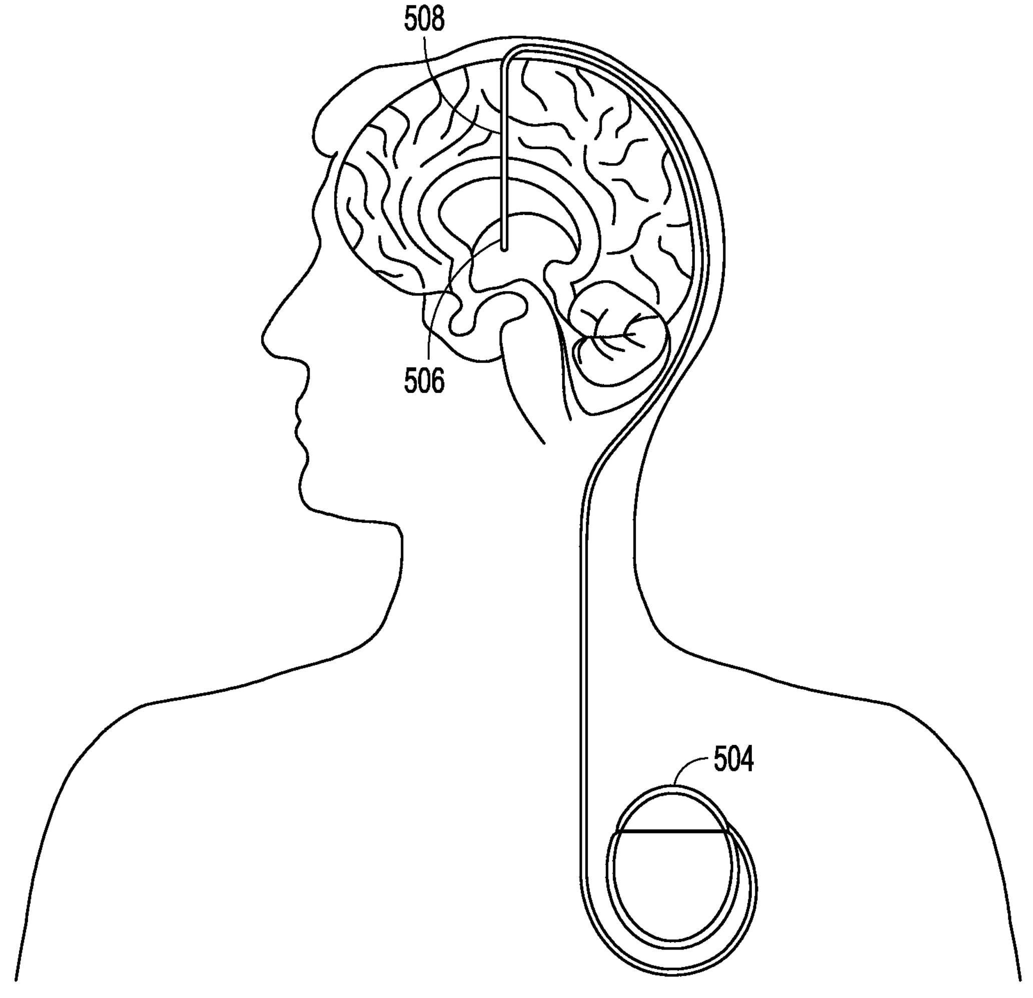
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), globus pallidus externus (GPe), medial forebrain bundle (MFB), periaquaductal gray (PAG), periventricular gray (PVG), habenula, subgenual cingulate cortex, ventral intermediate nucleus (VIM) of the thalamus, anterior nucleus (AN) or other nuclei of the thalamus, zona incerta, ventral capsule, ventral striatum, nucleus accumbens, and other white matter tracts connecting these and other structures. DBS is discussed as an example for the present subject matter, which can be applied to other brain stimulation (e.g., cortical stimulation) and other neurostimulation therapies.

Returning to FIG. 4, the IPG 404 can include a hermetically-sealed IPG case 422 to house the electronic circuitry of IPG 404. IPG 404 can include an electrode 426 formed on IPG case 422. In some embodiments, IPG case 422 can be used as electrode 426. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
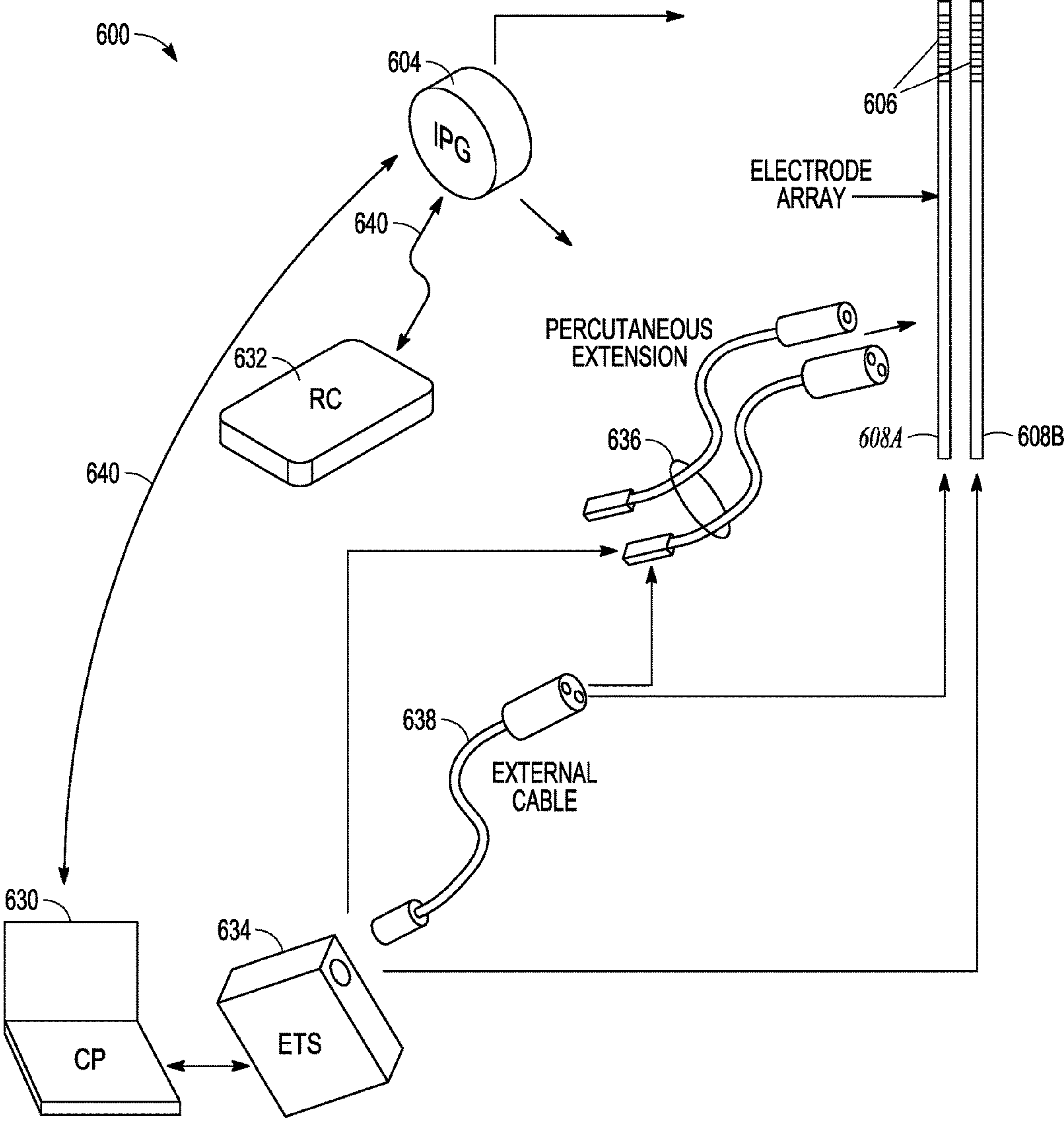
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS) 634. IPG 404 may be electrically coupled to leads 608A and 608B directly or through percutaneous extension leads 636 ETS 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $\lambda=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG-604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
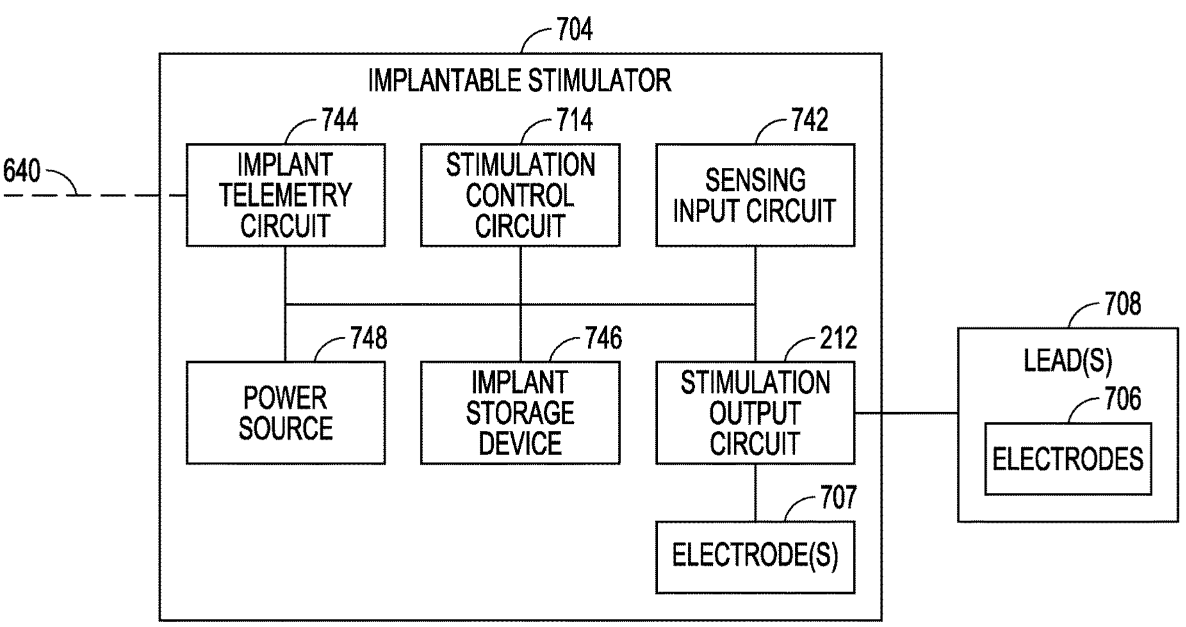
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing input circuit (also known as a sensing circuit) 742 that provides the stimulator with a sensing capability, stimulation output circuit 212, a stimulation control circuit 714, an implant storage device 746, an implant telemetry circuit 744, a power source 748, and one or more electrodes 707. Sensing input circuit 742 senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing input circuit 742.

In various embodiments, sensing input circuit 742, stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
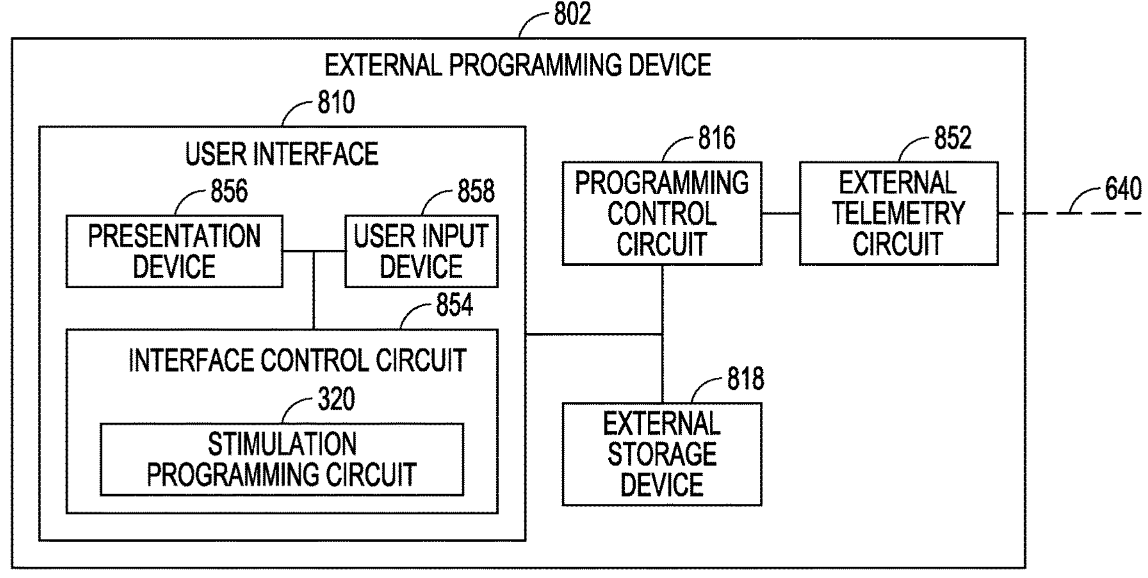
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on a specified stimulation configuration (e.g., the pattern of neurostimulation pulses as represented by one or more stimulation waveforms and one or more stimulation fields, or at least certain aspects of the pattern). The stimulation configuration may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation programming circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

FIGS. 9A-9E and 10A-10C illustrate embodiments of "parameter dithering", which produces an average value for a stimulation parameter by interleaving a higher value with a lower value at a calculated ratio. When delivery of neurostimulation pulses is controlled using stimulation parameters, a desired value of a stimulation parameter can be "dithered" by delivering neurostimulation pulses that interleaves M pulses at a higher value of a stimulation parameter with N pulses at a lower value of the stimulation parameter (at the radio of M:N) periodically at a period of M+N pulses so as to produce an average value that approximates the desired value. The average value equals (M×the higher value)+(N×the lower value)/(M+N). While pulse amplitude and pulse width are specifically discussed as examples of the stimulation parameters, the parameter dithering can also be applied to other stimulation parameters such as pulse frequency (also referred to as pulse rate, stimulation frequency, or stimulation rate).

Parameter dithering is needed only when a desired resolution of at least one stimulation parameter is higher than the hardware limitation of the stimulation output circuit (e.g., stimulation output circuit 212) used to deliver the neurostimulation pulses. The hardware limitation determines a "hardware resolution". The hardware resolution for a stimulation parameter is the minimum step for adjusting that stimulation parameter that can be achieved without modifying hardware and without applying the dithering according to the present subject matter.

FIGS. 9A-9E illustrate an embodiment of dithering a pulse amplitude of neurostimulation pulses, with the following values used as an example for illustrative purposes:

- desired values for the pulse amplitude: 325 μA, 350 μA, and 375 μA;
- hardware resolution: 100 μA; and
- the higher and lower values closest to the desired values and available within the hardware resolution: 400 μA and 300 μA, respectively.

Figures 9A, 9B, 9C:
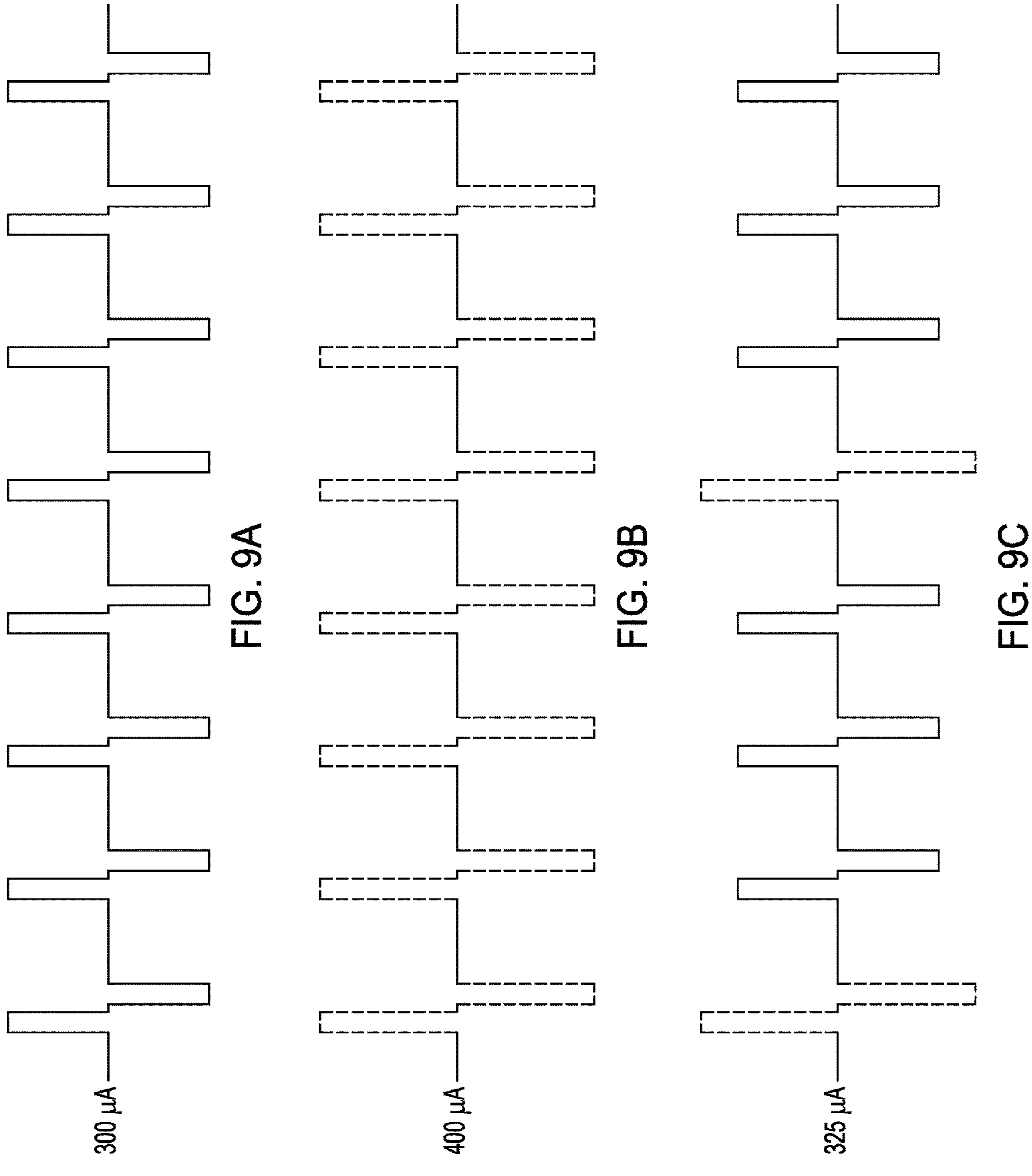
FIGS. 9A-9E illustrate an embodiment of dithering a pulse amplitude of neurostimulation pulses, with FIG. 9A showing an example of pulses having a first amplitude, FIG. 9B showing an example of pulses having a second amplitude, FIG. 9C showing an example of pulses having a third amplitude dithered using the first and second amplitudes, FIG. 9D showing an example of pulses having a fourth amplitude dithered using the first and second amplitudes, and FIG. 9E showing an example of pulses having a fifth amplitude dithered using the first and second amplitudes.

FIG. 9A shows an example of pulses having the pulse amplitude of 300 μA (the lower value). FIG. 9B shows an example of pulses having the pulse amplitude of 400 μA (the higher value). For dithering the pulse amplitude to provide each of the desired values, the neurostimulation can be delivered according to a pattern of neurostimulation pulses that interleaves M pulses at the pulse amplitude of 400 μA with N pulses at the pulse amplitude of 300 μA (at the radio of M:N) periodically at a period of M+N pulses.

FIG. 9C shows an example of pulses having an average pulse amplitude of the first desired value, 325 μA. This is achieved by interleaving 1 pulse at the pulse amplitude of 400 μA with 3 pulses at the pulse amplitude of 300 μA (at the radio of 1:3) periodically at a period of 4 pulses.

Figures 9D, 9E:
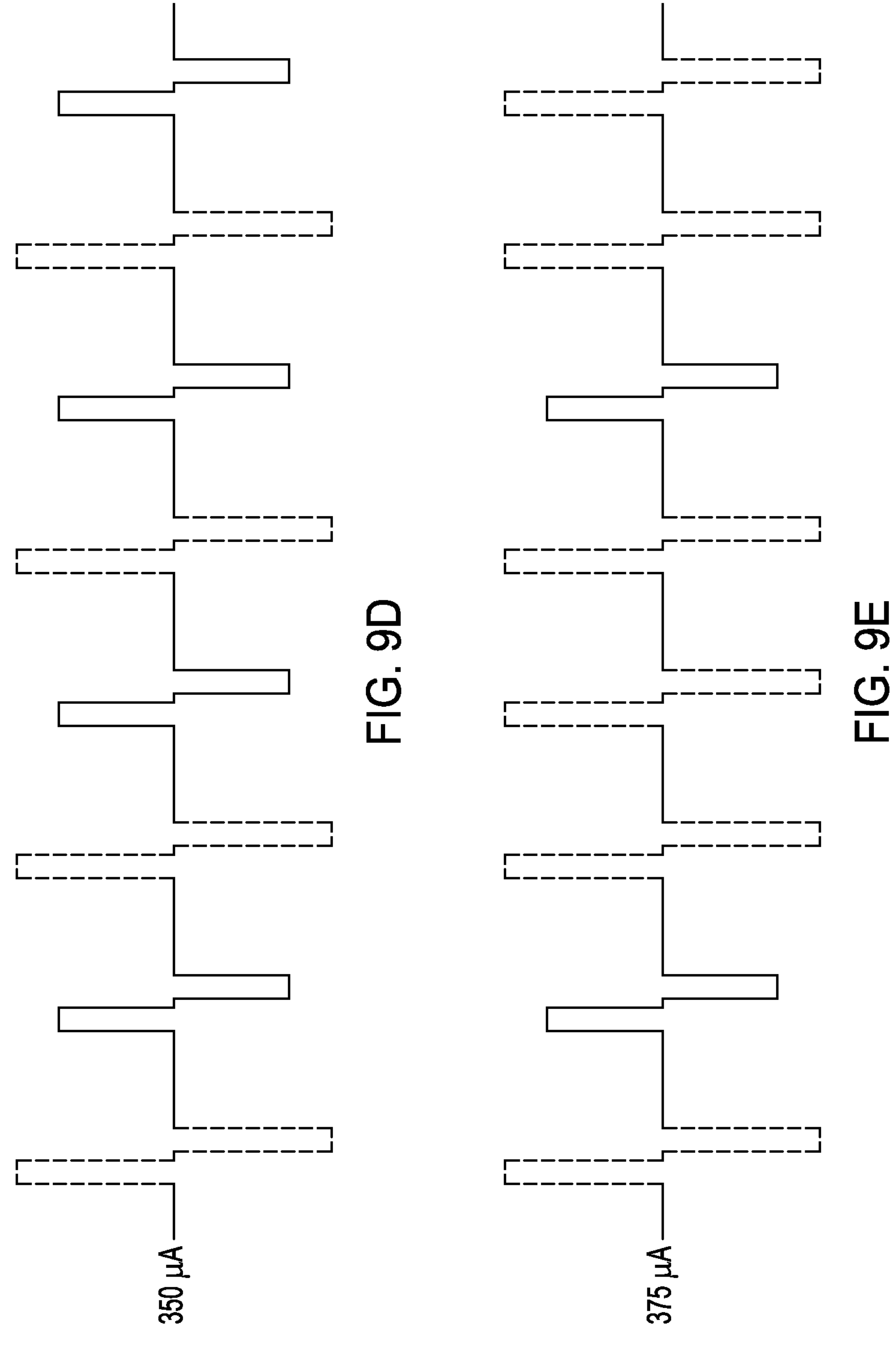

FIG. 9D shows an example of pulses having an average pulse amplitude of the second desired value, 350 μA. This is achieved by interleaving 1 pulse at the pulse amplitude of 400 μA with 1 pulse at the pulse amplitude of 300 μA (at the radio of 1:1) periodically at a period of 2 pulses.

FIG. 9E shows an example of pulses having an average pulse amplitude of the third desired value, 375 μA. This is achieved by interleaving 3 pulses at the pulse amplitude of 400 μA with 1 pulse at the pulse amplitude of 300 μA (at the radio of 3:1) periodically at a period of 4 pulses.

In this example, without the parameter dithering (i.e., with the hardware resolution), the step from 300 μA to 400 μA represents a 33% increase. With the parameter dithering, the step from 300 μA to 325 μA represents an 8.3% increase, the step from 325 μA to 350 μA represents an 7.7% increase, the step from 350 μA to 375 μA represents a 7.1% increase, and the step from 375 μA to 400 μA represents a 6.0% increase. In such a manner, the parameter dithering improves the resolution of the pulse amplitude without modifying the hardware of the stimulation output circuit.

Figures 10A, 10B, 10C:
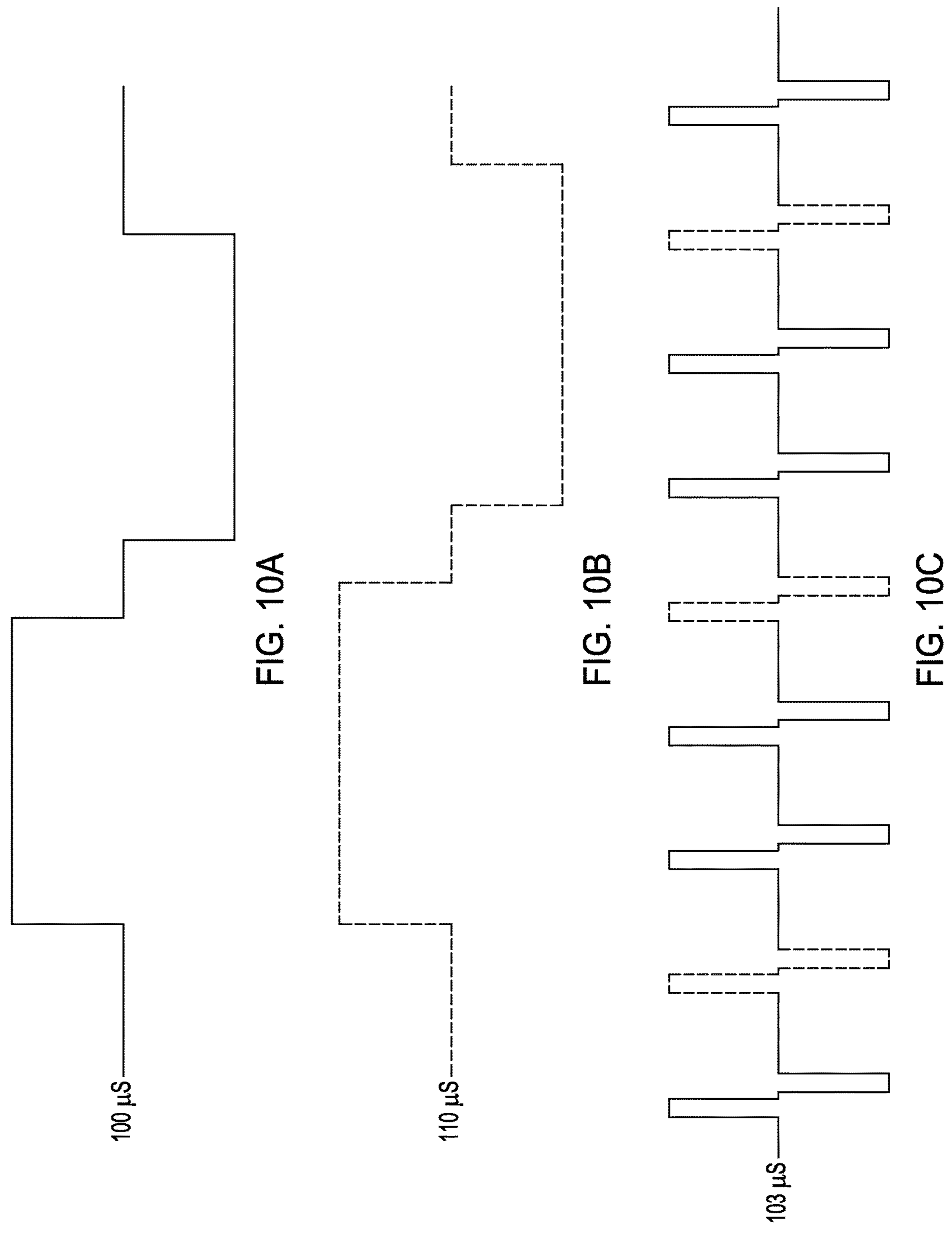
FIGS. 10A-10C illustrate an embodiment of dithering a pulse width of neurostimulation pulses, with FIG. 10A showing an example of a pulse having a first pulse width, FIG. 10B showing an example of a pulse having a second pulse width, and FIG. 10C showing an example of pulses having a third pulse width dithered using the first and second pulse widths.

FIGS. 10A-10C illustrate an embodiment of dithering a pulse width of neurostimulation pulses, with the following values used as an example for illustrative purposes:

- desired value for the pulse width: 103 μs;
- hardware resolution: 110 μs; and
- the higher and lower values closest to the desired values and available within the hardware resolution: 110 μs and 100 μs, respectively.

FIG. 10A shows an example of pulses having the pulse width of 100 μs (the lower value). FIG. 10B shows an example of pulses having the pulse width of 110 μs (the higher value). For dithering the pulse width to provide the desired value, the neurostimulation can be delivered according to a pattern of neurostimulation pulses that interleaves M pulses at the pulse amplitude of 110 us with N pulses at the pulse amplitude of 100 μs (at the radio of M:N) periodically at a period of M+N pulses.

FIG. 10C shows an example of pulses having an average pulse width of the desired value, 103 μs. This is achieved by interleaving 1 pulse at the pulse amplitude of 110 μs with 2 pulses at the pulse amplitude of 100 μs (at the radio of 1:2) periodically at a period of 3 pulses.

In this example, without the parameter dithering (i.e., with the hardware resolution), the step from 100 μs to 110 μs represents a 10% increase. With the parameter dithering, the step from 100 μs to 103 μs represents an 3% increase. In such a manner, the parameter dithering improves the resolution of the pulse width without modifying the hardware of the stimulation output circuit.

Figure 11:
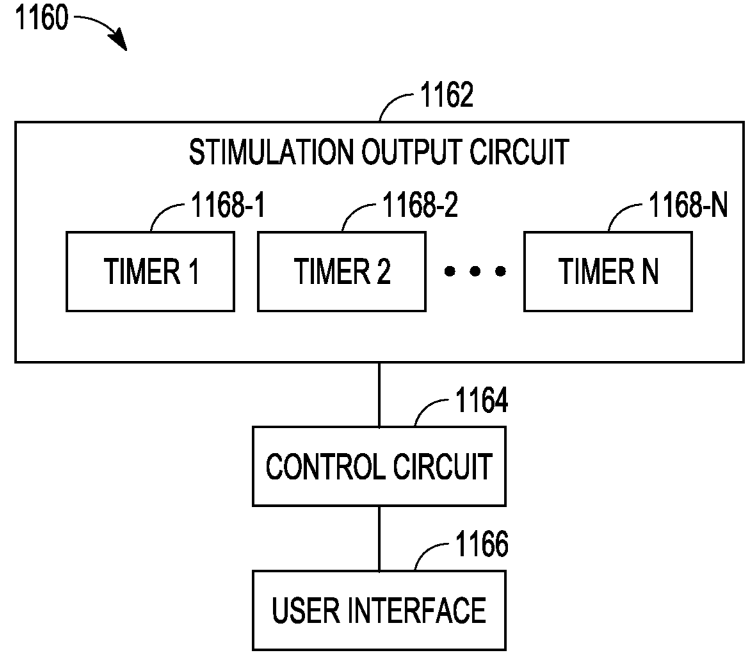
FIG. 11 illustrates an embodiment of a system for delivering neurostimulation pulses and controlling the delivery of the neurostimulation pulses.

FIG. 11 illustrates an embodiment of a system 1160 for delivering neurostimulation pulses and controlling the delivery of the neurostimulation pulses. System 1160 can include a stimulation output circuit 1162, a control circuit 1164, and a user interface 1166. System 1160, including the various embodiments of its components, can be implemented in any suitable neurostimulation systems, including but not limited to those discussed above, such as systems 100 and 600 (including the various embodiments of their components as discussed above). For example, stimulation output circuit 1162 can be implemented in stimulation output circuit 212, control circuit 1164 can be implemented in stimulation programming circuit 320 and/or stimulation control circuit 714, and user interface 1166 can be implemented in user interface 810. In other words, stimulation output circuit 212 can be configured to include stimulation output circuit 1162, stimulation programming circuit 320 and/or stimulation control circuit 714 can be configured (e.g., programmed) to include control circuit 1164, and user interface 810 can be configured (e.g., programmed) to perform the functions of user interface 1166.

Stimulation output circuit 1162 can deliver neurostimulation according to stimulation parameters defining a pattern of neurostimulation pulses. Stimulation output circuit 1162 sets a hardware resolution for each parameter of the stimulation parameters. The hardware resolution is a minimum step size for adjusting the value of each stimulation parameter. In one example (as used in FIGS. 9A-9E and 10A-10C) the hardware resolution includes 100 μA for pulse amplitude and 10 μs for pulse width. Stimulation output circuit includes N timers 1168: timer 1168-1, timer 1168-2, . . . timer 1168-N. Timers (also known as "channels" or "timing channels") 1168 are each independently operable to control timing of one or more pulses of the pattern of neurostimulation pulses. Pulses delivered to each stimulation field (electrode set) is the sum of pulses controlled by all the timers employed for this stimulation field. Timers 1168 are part of the hardware of stimulation output circuit 1162 and can be programmed according to the pattern of neurostimulation pulses. The number of timers (N) available in stimulation output circuit 1162 determines the highest resolution (smallest step for adjusting a stimulation parameter) achievable with the stimulation device having stimulation output circuit 1162 when the parameter dithering is applied. With the parameter dithering according to the present subject matter, without modifying hardware of a stimulation device, the highest resolution for setting stimulation parameters achievable depends on the number of timers configurable by programming that stimulation device.

In the Examples shown in FIGS. 9A-9E, one timer is required for each 400 μA pulse and one timer is required for each 300 μA pulse during each period of M+N pulses. For the example of FIG. 9C, 4 timers are required, including 1 for the 400 μA pulse and 3 for the 300 μA pulses for the 4-pulse period. For the example of FIG. 9D, 2 timers are required, including 1 for the 400 μA pulse and 1 for the 300 μA pulse for the 2-pulse period. For the example of FIG. 9E, 4 timers are required, including 3 for the 400 μA pulses and 1 for the 300 μA pulse for the 4-pulse period. In the Examples shown in FIGS. 10A-10C, one timer is required for each 110-μs pulse and one timer is required for each 100-μs pulse during each period of M+N pulses. For the example of FIG. 10C, 3 timers are required, including 1 for the 110-μs pulse and 2 for the 100-μs pulses for the 3-pulse period.

Control circuit 1164 can control operation of stimulation output circuit 1162, including operation of the timers 1168. User interface 1166 allows the user to control the delivery of neurostimulation by, for example, composing the pattern of neurostimulation pulses, including setting and adjusting the stimulation parameters defining the pattern of neurostimulation pulses. When stimulation output circuit 1162 is part of an implantable device (e.g., implantable stimulator 704), control circuit 1164 can include part of circuitry of the implantable device (e.g., part of stimulation control circuit 714) and/or part of circuitry of a programmer (e.g., part of stimulation programming circuit 320 of external programming device 802). User interface 1155 is part of the programmer (e.g., user interface 810). In various embodiments, control circuit 1164 and user interface 1166 are configured (e.g., programmed) to provide system 1160 with capability of performing the parameter dithering.

Figure 12:
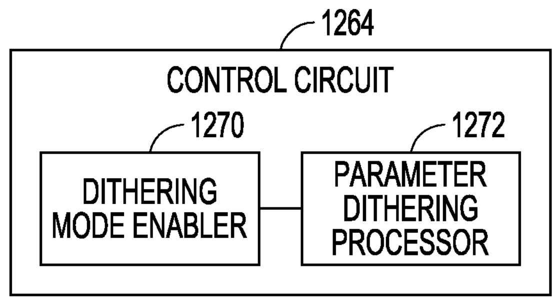
FIG. 12 illustrates an embodiment of a control circuit capable of parameter dithering in a neurostimulation system, such as the system of FIG. 11.

FIG. 12 illustrates an embodiment of a control circuit 1264. Control circuit 1264 represents an embodiment of control circuit 1164 and is capable of processing stimulation parameters under a dithering mode in a neurostimulation system, such as system 1160. Control circuit 1264 can receive stimulation parameters and control operation of a stimulation output circuit having timers (e.g., stimulation output circuit 1162 having timers 1168) using the received stimulation parameters. In various embodiments, control circuit 1264 can be configured to operate under a dithering mode and performs the parameter dithering (e.g., as discussed above with reference to FIGS. 9A-9E and 10A-10C) when the dithering mode is enabled. In the illustrated embodiment, control circuit 1264 includes a dithering mode enabler 1270 and a parameter dithering processor 1272. Dithering mode enabler 1270 can be configured to enable the dithering mode. Parameter dithering processor 1272 can be configured to operate when the dithering mode is enabled, to identify a stimulation parameter from the received stimulation parameters to be dithered, the identified stimulation parameter having a received value that is not available with the hardware resolution, and to dither the received value. Parameter dithering processor 1272 can dither the received value by programming the stimulation output circuit (e.g., stimulation output circuit 1162) to deliver neurostimulation pulses at a higher value of the identified stimulation parameter interleaved with neurostimulation pulses at a lower value of the identified parameter at a ratio determined for producing an average value approximating to the received value. The higher value and the lower value are values of the identified stimulation parameter that are available with the hardware resolution.

In various embodiments, dithering mode enabler 1270 can execute an algorithm determining whether to enable the dithering mode based one or more criteria such as whether the parameter dithering is need based on values of the received stimulation parameters, a user selection (e.g., between using the dithering mode and modifying values of the stimulation parameters to avoid the need for using the dithering mode), and/or other factors (e.g., additional power consumption, processing time, and/or computational resources needed for operating under the dithering mode).

In various embodiments, dithering mode enabler 1270 determines whether the parameter dithering is needed and enables the dithering mode in response to the determination that the parameter dithering is needed. If the dithering mode is already enabled, dithering mode enabler 1270 can keep the dithering mode enabled in response to the determination that the parameter dithering is needed and disable the dithering mode in response to the determination that the parameter dithering is not needed. This avoids unnecessary application of the parameter dithering, which can be preferably to be applied only when it is necessary to overcome hardware limits to a certain extent. In one embodiment, dithering mode enabler 1270 determines whether the hardware resolution is sufficient for values of the received stimulation parameters without enabling the dithering mode. This can include determining a desirable maximum relative step size for a stimulation parameter of the received stimulation parameters based on received values of that stimulation parameter. The maximum relative step size can be specified, for example, as a percentage for a value of the stimulation parameter. If the hardware resolution is sufficient for the desirable maximum relative step size, the parameter dithering is not needed. If the hardware resolution is not sufficient for the desirable maximum relative step size, the parameter dithering is needed.

In an example (herein referred to as "the 100 μA-5% example") to be discussed below for illustrative purposes, the desirable maximum relative step size is 5% for a pulse amplitude. The hardware resolution of 100 μA is sufficient for a 5% step size for the pulse amplitude of 2 mA. The parameter dithering is needed when the 5% step size is smaller than 100 μA.

In various embodiments, dithering mode enabler 1270 enables the dithering mode in response to a determination that the hardware resolution is not sufficient for at least one value of the received stimulation parameters without enabling the dithering mode. Dithering mode enabler 1270 can determine whether the hardware resolution is sufficient for the values of the received stimulation parameters with the dithering mode enabled and enable the dithering mode in response to a determination that the hardware resolution is not sufficient for at least one value of the received stimulation parameters without enabling the dithering mode and is sufficient for the values of the received stimulation parameters with the dithering mode enabled. In response to a determination that the hardware resolution is not sufficient for at least one value of the received stimulation parameters even with the dithering mode enabled, dithering mode enabler 1270 can inform the user, for example using user interface 1166, of a need for modifying one or more values of the stimulation parameters.

In various embodiments, dithering mode enabler 1270 allows the user to select a parameter dithering option and enables the dithering mode in response to the selection of the parameter dithering option. When the hardware limitation is not sufficient for the values of the received stimulation parameters, this allows the user to choose between modifying the stimulation parameters and applying the parameter dithering. User interface 1166 can be used to receive the selection from the user. For example, when user interface 1155 is implemented in user interface 810 (including presentation device 856 and user input device 858), dithering mode enabler 1270 can present the parameter dithering option using presentation device 856, receive a selection of the parameter dithering option using user input device 858, and enable the dithering mode in response to the selection of the parameter dithering option being received. Dithering mode enabler 1270 can further allow the user to disable the dithering mode using user interface 1166 when the dithering mode is enabled, for example by deselecting the parameter dithering option.

In various embodiments, dithering mode enabler 1270 allows the user to select the parameter dithering option in response to the determination that the parameter dithering is needed. In various embodiments, dithering mode enabler 1270 enables the dithering mode in response to the determination that the parameter dithering is needed and the selection of the parameter dithering option.

Parameter dithering processor 1272 can be configured to operate when the dithering mode is enabled. In various embodiments, parameter dithering processor 1272 identifies a stimulation parameter from the received stimulation parameters to be dithered. The identified stimulation parameter has a received value that is not available with the hardware resolution. Then, parameter dithering processor 1272 dithers the received value by programming stimulation output circuit 1162 to deliver neurostimulation pulses at a higher value of the identified stimulation parameter interleaved with neurostimulation pulses at a lower value of the identified parameter at a ratio determined for producing an average value approximating to the received value. The higher value and the lower value are values of the identified stimulation parameter that are available with the hardware resolution. In other words, parameter dithering processor 1272 dithers the received value by programming stimulation output circuit 1162 to deliver neurostimulation pulses with the identified stimulation parameter having a higher value interleaved with a lower value at a ratio determined for producing an average value approximating to the received value. The higher value and the lower value are values of the identified stimulation parameter that are available with the hardware resolution. The ratio is a function of the number of timers 1168 used to control the delivery of the neurostimulation pulses with the identified stimulation parameter having the higher value interleaved with the lower value. In various embodiments, parameter dithering processor 1272 determines a minimum number of timers 1168 required based on the desirable maximum relative step size, determines the ratio based on the minimum number of timers 1168 used to dither the received value, and controls the delivery of the neurostimulation by using the minimum number of timers for the identified stimulation parameter.

Figure 13:
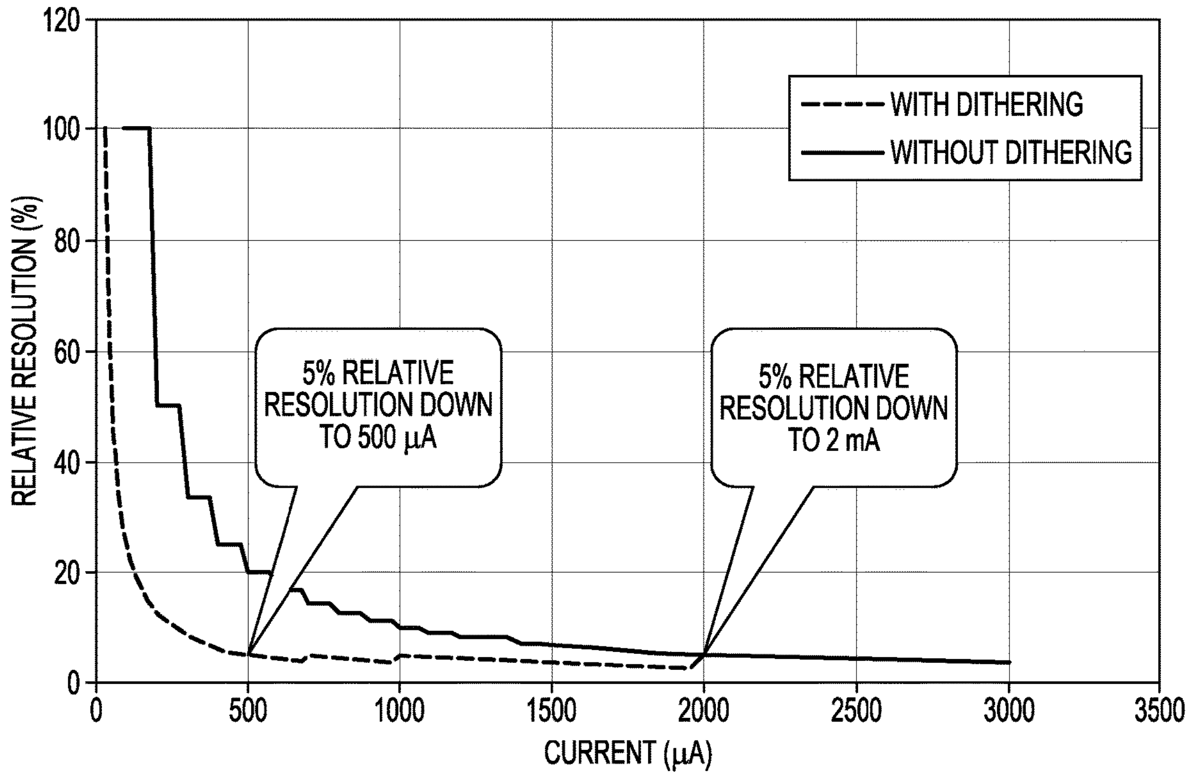
FIG. 13 illustrates an example of relative resolutions for a pulse amplitude achieved with and without parameter dithering.

FIG. 13 illustrates, using the 100 μA-5% example, the relative resolutions for a pulse amplitude achieved with and without parameter dithering. The minimum number of timers 1168 can be determined, for example, by determining breakpoints at which the relative step size exceeds the desirable maximum relative step size (thereby requiring an additional timer). In the 100 μA-5% example, the breakpoints with 1-4 timers are as follows:

- 1 timer (providing 100 μA steps); 100 μA/5%=2 μA (1 timer needed, i.e., no dithering needed, for 2 μA and above);
- 2 timers (providing 50 μA steps): 50 μA/5%=1000 μA, maximum amplitude 2 μA−50 μA=1950 μA (2 timers needed for 1000 μA to 1950 μA);
- 3 timers (providing 33 μA steps): 33 μA/5%=660 μA, maximum amplitude 1000 μA−33 μA=967 μA (3 timers needed for 660 μA to 967 μA); and
- 4 timers (providing 25 μA steps): 25 μA/5%=500 μA maximum amplitude 660 μA−25 μA=645 μA (4 timers needed for 500 μA to 645 μA).

This can repeat until all available timers have been used. The number of available timers determines the smallest breakpoint/finest resolution achievable. FIG. 13 shows the relative resolution achievable with 1 timer (the "WITHOUT DITHERING" curve) and the relative resolution achievable with 4 timers (the "WITH DITHERING" curve). With 4 timers, a 5% relative amplitude step size can be achieved for a pulse amplitude down to 500 μA (compared to 2 mA with 1 timer, i.e., the hardware resolution).

System 1160 can be implemented in various neurostimulation systems each including an implantable stimulator and an external programming device. Depending on specific system platforms, additional features needed for implementing the parameter dithering can be included in the implantable stimulator (e.g., implantable stimulator 704) and/or the external programming device (e.g., external programming device 802). In one example, control circuit 1164 is primarily or totally implemented in implantable stimulator 704. This can be done by modifying firmware of implantable stimulator 704 to include control circuit 1164 (or at least major portions control circuit 1164) in stimulation control circuit 714 and, when needed, to add timers in stimulation output circuit 212. External programming device 802 is modified to include additional features of user interface 810 needed to support the parameter dithering option. Programming control circuit 816 transmits information including data representing the stimulation parameters as received, without dithering, to implantable stimulator 704. In another example, control circuit 1164 is primarily or totally implemented in external programming device 802. No modification of implantable stimulator 704 is needed. External programming device 802 is modified to include control circuit 1164 (or at least major portions control circuit 1164) in stimulation programming circuit 320 and to include additional features of user interface 810 needed to support the parameter dithering option. Programming control circuit 816 transmits information including data representing the stimulation parameters as dithered, when the dithering mode is enabled and used.

In various embodiments, circuits of systems 100, 600, and 1160, including their various embodiments discussed in this document, may be implemented using a combination of hardware and software. For example, the circuit of user interface 110, stimulation output circuit 212, stimulation control circuit 214, programming control circuit 316, and stimulation programming circuit 320, sensing circuit 742, stimulation control circuit 714, implant telemetry circuit 744, external telemetry circuit 852, programming control circuit 816, interface control circuit 854, stimulation output circuit 1162, control circuit 1164, and control circuit 1264, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 14:
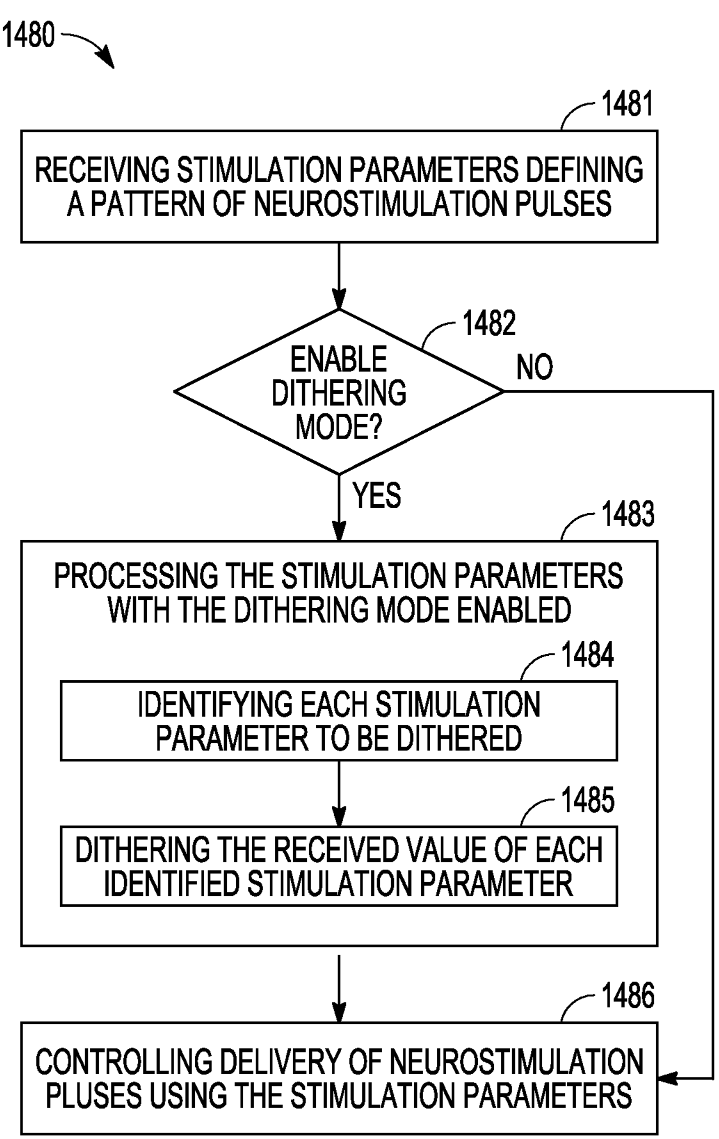
FIG. 14 illustrates an embodiment of a method for controlling delivery of the neurostimulation pulses that includes parameter dithering when needed.

FIG. 14 illustrates an embodiment of a method 1480 for controlling delivery of the neurostimulation pulses that includes parameter dithering when needed. Method 1480 can be performed to deliver neurostimulation according a pattern of neurostimulation pulses using system 1160 when system 1160 is implemented in a neurostimulation system such as system 100 or 600, including the various embodiments of their components as discussed in this document. In various embodiments, a non-transitory computer-readable storage medium includes instructions, which when executed by a system (e.g., system 1160), cause the system to perform method 1480. Examples of such storage medium include implant storage device 746, external storage device 818, any storage medium used for configuring (e.g., programming) an implantable stimulator (e.g., implantable stimulator 704) and/or external programming device (e.g., external programming device 802), or any combination of these storage media.

Method 1480 can be performed for delivering neurostimulation from a stimulation output circuit according a pattern of neurostimulation pulses. At 1481, stimulation parameters defining the pattern of neurostimulation pulses are received. At 1482, whether to enable a dithering mode is determined using one or more criteria. Examples of the one or more criteria include whether parameter dithering is needed based on a hardware resolution of the stimulation output circuit and values of the received stimulation parameters, whether a parameter dithering option is selected by a user, and one or more other factors (e.g., additional power, time, and/or computational resources needed for the parameter dithering). In various embodiments, the dithering mode is to be enabled in response to the determination that the parameter dithering is needed and/or the determination that the parameter dithering option is selected by the user.

If the dithering mode is not to be enabled at 1482, delivery of the neurostimulation pulses is controlled using the received stimulation parameter (i.e., the stimulation parameters with their values as received at 1481) at 1486.

If the dithering mode is to be enabled at 1482, the stimulation parameters are processed with the dithering mode enabled at 1483. This includes identify each stimulation parameter to be dithered, at 1484, and dithering the received value of each identified stimulation parameter, at 1485. At 1484, each stimulation parameter having a received value that needs to be dithers is identified from the received stimulation parameters. Each identified stimulation parameter has a received value that is not available with a hardware resolution set by the stimulation output circuit for that stimulation parameter. At 1485, the received value of each identified stimulation parameter is dithered by programming the stimulation output circuit to deliver neurostimulation pulses at a higher value of the identified stimulation parameter interleaved with neurostimulation pulses at a lower value of the identified parameter at a ratio determined for producing an average value approximating to the received value. The higher value and the lower value are values of the identified stimulation parameter that are available with the hardware resolution. At 1486, delivery of the neurostimulation pulses are controlled using the processed stimulation parameters (i.e., the stimulation parameters with values of the identified stimulation parameters dithered at 1485).

In various embodiments, at 1485, the ratio for producing the average value approximating to the received value is determined as a function of the number of timers used to control the delivery of the neurostimulation pulses using the identified stimulation parameter when the dithering mode is enabled. The timers are part of the stimulation output circuit and are each independently programmable for controlling timing of one or more pulses of the pattern of neurostimulation pulses. The determination of the ratio can include determining a desirable maximum relative step size for the identified stimulation parameter, determining a minimum number of the timers required based on the determined desirable maximum relative step size for the identified stimulation parameter and the hardware resolution, and setting the ratio based on the determined minimum number of the timers.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation from a stimulation output circuit according to stimulation parameters defining a pattern of neurostimulation pulses, the stimulation output circuit setting a hardware resolution for each parameter of the stimulation parameters and including timers each independently programmable for controlling timing of one or more pulses of the pattern of neurostimulation pulses, the system comprising:

a control circuit configured to receive the stimulation parameters and to control operation of the stimulation output circuit using the received stimulation parameters, the control circuit including:

a dithering mode enabler configured to enable a dithering mode; and a parameter dithering processor configured to:

operate when the dithering mode is enabled;

identify a stimulation parameter from the received stimulation parameters to be dithered, the identified stimulation parameter having a received value that is not available with the hardware resolution; and dither the received value by programming the stimulation output circuit to deliver neurostimulation pulses at a higher value of the identified stimulation parameter interleaved with neurostimulation pulses at a lower value of the identified stimulation parameter at a ratio determined for producing an average value approximating to the received value, the higher value and the lower value being values of the identified stimulation parameter that are available with the hardware resolution.

2. The system of claim 1, wherein the dithering mode enabler is configured to determine whether parameter dithering is needed and to enable the dithering mode in response to the determination that the parameter dithering is needed.

3. The system of claim 2, wherein the dithering mode enabler is configured to determine whether the hardware resolution is sufficient for values of the received stimulation parameters without enabling the dithering mode and to enable the dithering mode in response to the determination that the hardware resolution is not sufficient for at least one value of the received stimulation parameters without enabling the dithering mode.

4. The system of claim 3, wherein the dithering mode enabler is configured to determine a desirable maximum relative step size for each stimulation parameter of the received stimulation parameters based on received values of that stimulation parameter and to determine whether the hardware resolution is sufficient for the determined desirable maximum relative step sizes of all the received stimulation parameters.

5. The system of claim 3, wherein the dithering mode enabler is configured to determine whether the hardware resolution is sufficient for the values of the received stimulation parameters with the dithering mode enabled and to enable the dithering mode in response to the determination that the hardware resolution is not sufficient for at least one value of the received stimulation parameters without enabling the dithering mode and a determination that the hardware resolution is sufficient for the values of the received stimulation parameters with the dithering mode enabled.

6. The system of claim 2, further comprising a user interface, and wherein the dithering mode enabler is further configured to allow for a selection of a parameter dithering option using the user interface and to enable the dithering mode in response to the selection of the parameter dithering option.

7. The system of claim 6, wherein the dithering mode enabler is configured to enable the dithering mode in response to the determination that the parameter dithering is needed and the selection of the parameter dithering option.

8. The system of claim 1, wherein the parameter dithering processor is configured to determine the ratio being a function of a number of the timers used to control the delivery of the neurostimulation pulses using the identified stimulation parameter when the dithering mode is enabled.

9. The system of claim 8, wherein the parameter dithering processor is configured to determine a desirable maximum relative step size for the identified stimulation parameter, to determine a minimum number of the timers required based on the determined desirable maximum relative step size for the identified stimulation parameter and the hardware resolution, and to set the ratio based on the determined minimum number of the timers.

10. The system of claim 9, wherein the parameter dithering processor is configured to determine the minimum number of the timers by determining breaking points at which a step size for the identified obtained using a given number of the timers exceeds the desirable maximum relative step size for the identified stimulation parameter, the breaking points each indicating a need for an additional timer.

11. A method for delivering neurostimulation from a stimulation output circuit according to a pattern of neurostimulation pulses, the method comprising:

receiving stimulation parameters defining the pattern of neurostimulation pulses;

determining whether to enable a dithering mode using one or more criteria;

enabling the dithering mode when the one or more criteria are met;

processing the received stimulation parameters using a processor, the processing when the dithering mode is enabled including:

identifying a stimulation parameter from the received stimulation parameters to be dithered, the identified stimulation parameter having a received value that is not available with a hardware resolution set by the stimulation output circuit for each parameter of the received stimulation parameters; and dithering the received value by programming the stimulation output circuit to deliver neurostimulation pulses at a higher value of the identified stimulation parameter interleaved with neurostimulation pulses at a lower value of the identified stimulation parameter at a ratio determined for producing an average value approximating to the received value, the higher value and the lower value being values of the identified stimulation parameter that are available with the hardware resolution; and controlling operation of the stimulation output circuit using the processed stimulation parameters.

12. The method of claim 11, wherein determining whether to enable the dithering mode comprises determining whether parameter dithering is needed.

13. The method of claim 12, wherein determining whether the parameter dithering is needed comprises determining whether the hardware resolution is sufficient for all values of each stimulation parameter of the received stimulation parameters without enabling the dithering mode.

14. The method of claim 13, wherein determining whether to enable the dithering mode comprises determining whether the hardware resolution is sufficient for all values of each stimulation parameter of the received stimulation parameters with the dithering mode enabled.

15. The method of claim 12, wherein determining whether to enable the dithering mode comprises determining whether a parameter dithering option is selected by a user.

16. The method of claim 15, wherein enabling the dithering mode comprises enabling the dithering mode in response to the determination that the parameter dithering is needed and the determination that the parameter dithering option is selected by the user.

17. The method of claim 11, further comprising determining the ratio as a function of a number of timers used to control the delivery of the neurostimulation pulses using the identified stimulation parameter when the dithering mode is enabled, the timers being part of the stimulation output circuit and each independently programmable for controlling timing of one or more pulses of the pattern of neurostimulation pulses.

18. The method of claim 17, wherein determining the ratio comprises:

determining a desirable maximum relative step size for the identified stimulation parameter;

determining a minimum number of the timers required based on the determined desirable maximum relative step size for the identified stimulation parameter and the hardware resolution; and setting the ratio based on the determined minimum number of the timers.

19. A non-transitory computer-readable storage medium including instructions, which when executed by a system, cause the system to perform a method for delivering neurostimulation from a stimulation output circuit according to a pattern of neurostimulation pulses, the method comprising:

receiving stimulation parameters defining the pattern of neurostimulation pulses;

determining whether to enable a dithering mode using one or more criteria;

enabling the dithering mode when the one or more criteria are met;

processing the received stimulation parameters using a processor, the processing when the dithering mode is enabled including:

identifying a stimulation parameter from the received stimulation parameters to be dithered, the identified stimulation parameter having a received value that is not available with a hardware resolution set by the stimulation output circuit for each parameter of the received stimulation parameters; and dithering the received value by programming the stimulation output circuit to deliver neurostimulation pulses at a higher value of the identified stimulation parameter interleaved with neurostimulation pulses at a lower value of the identified stimulation parameter at a ratio determined for producing an average value approximating to the received value, the higher value and the lower value being values of the identified stimulation parameter that are available with the hardware resolution; and controlling operation of the stimulation output circuit using the processed stimulation parameters.

20. The non-transitory computer-readable storage medium of claim 19, wherein determining whether to enable the dithering mode comprises at least one of determining whether parameter dithering is needed or whether a parameter dithering option is selected by a user.

* * * * *